United States Patent [19]

Osmont et al.

[11] Patent Number: 4,587,667
[45] Date of Patent: May 6, 1986

[54] METHOD AND APPARATUS FOR INSPECTION BY RADIOACTIVE GAGE OF A MOVING STRIP OF MATERIAL, IN PARTICULAR A STRIP OF RUBBER FOR TIRES

[75] Inventors: Gilles J. N. Osmont, Sartrouville; Jacques A. Y. Bourras-Laspelades, Villepinte, both of France

[73] Assignee: Sereg S.A., Montrouge, France

[21] Appl. No.: 566,379

[22] Filed: Dec. 28, 1983

[30] Foreign Application Priority Data

Dec. 29, 1982 [FR] France .............................. 82 21987

[51] Int. Cl.⁴ ............................................ G01N 23/00
[52] U.S. Cl. ....................................... 378/58; 378/61; 250/358.1
[58] Field of Search ............... 250/358.1, 359.1, 360.1; 378/54, 55, 56, 61

[56] References Cited

U.S. PATENT DOCUMENTS 3,125,680 3/1964 Schlaechter .
3,852,600 12/1974 Faulkner et al. ................. 250/358.1
4,047,036 9/1977 Smith et al. .

FOREIGN PATENT DOCUMENTS 0065361 11/1982 European Pat. Off. .
2226645 10/1975 France .
1252884 11/1971 United Kingdom .

OTHER PUBLICATIONS

"An Archiv fur Technisches Messen".
Robert C. McMaster—"Nondestructive Testing Handbook", 1959—vol. 1—pp. 1-33.

Primary Examiner—Janice A. Howell
Attorney, Agent, or Firm—Dale V. Gaudier

[57] ABSTRACT

A strip (B), generally trapezoidal in cross-section, traverses a measurement plane at the level of a line of passage (L). Two identical collimated radioactive sources (120, 121) are disposed to provide a substantially constant flux of radiation at the level of the line of passage (L). An elongate ionization chamber (310) receives at least all the radiation traversing the strip. The variations in the output signal of the ionization chamber indicate the presence in the strip of possible localized air inclusions or overweights.

The invention can be applied in particular to the inspection of rubber strip intended for the manufacture of tires.

15 Claims, 8 Drawing Figures

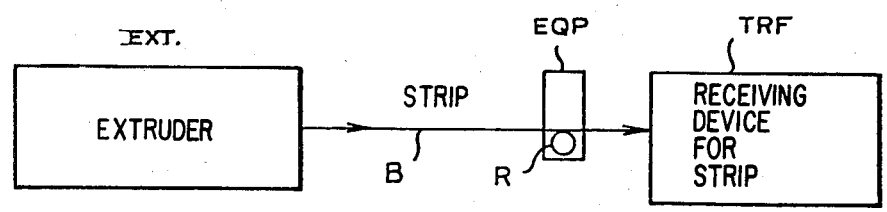
FIG_1
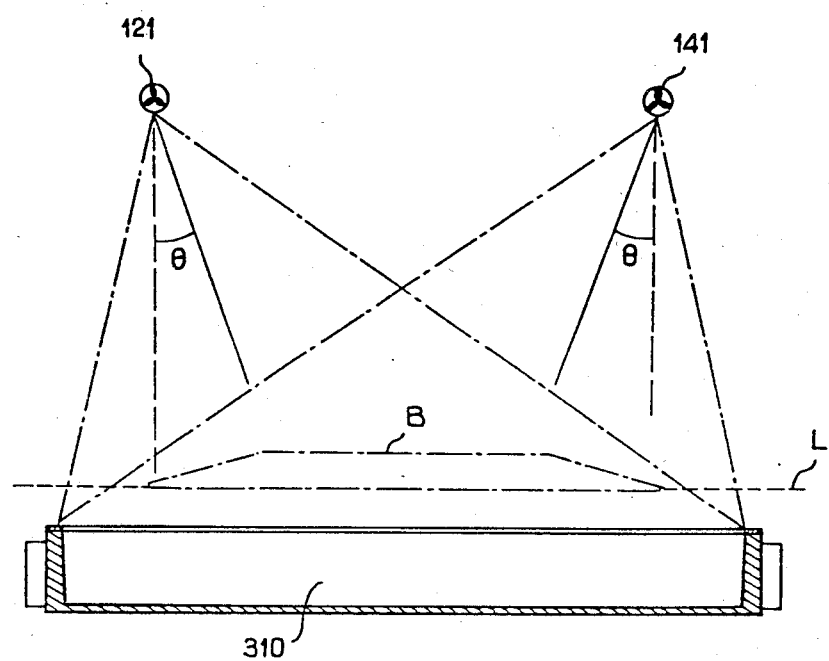
FIG_2

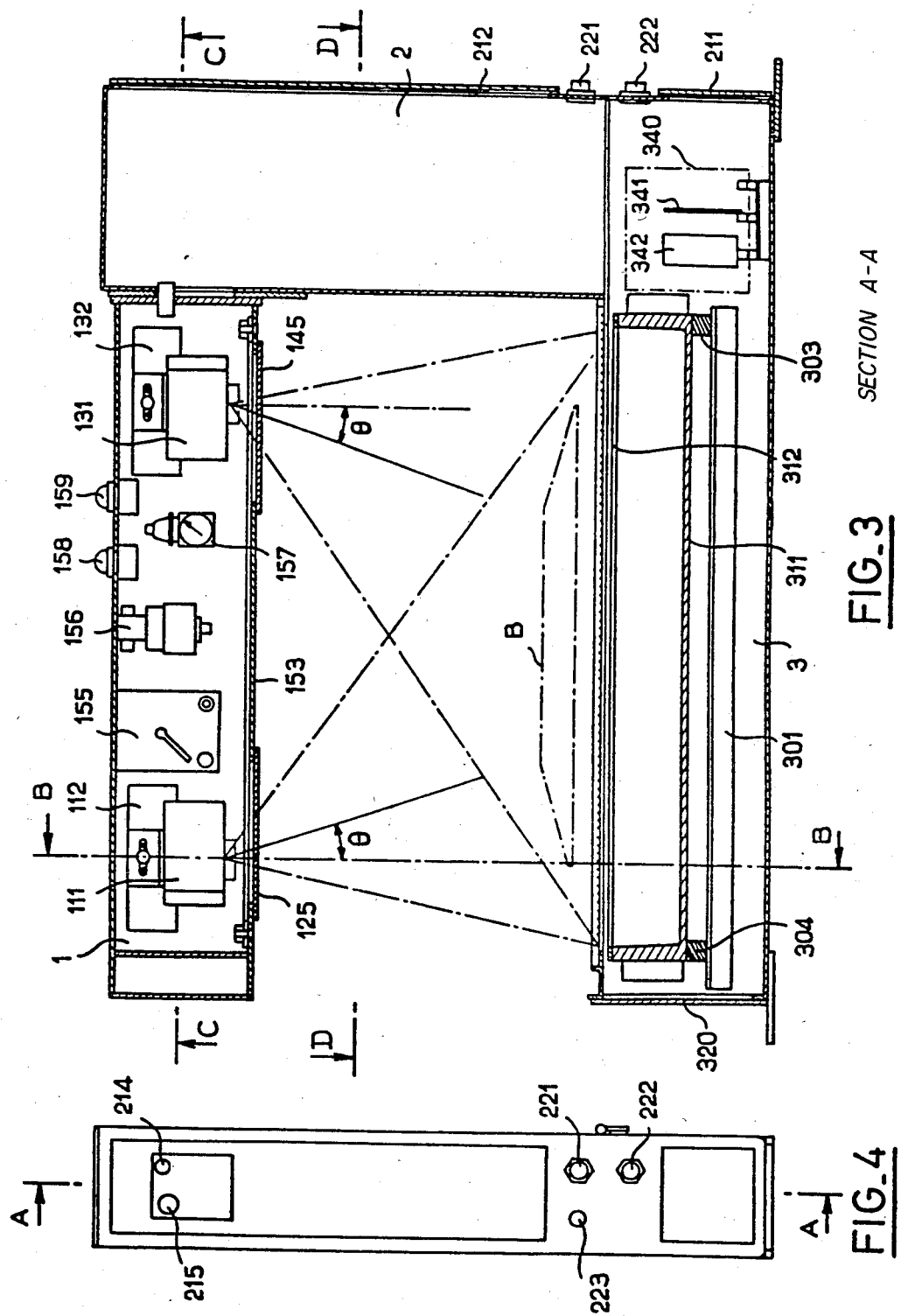

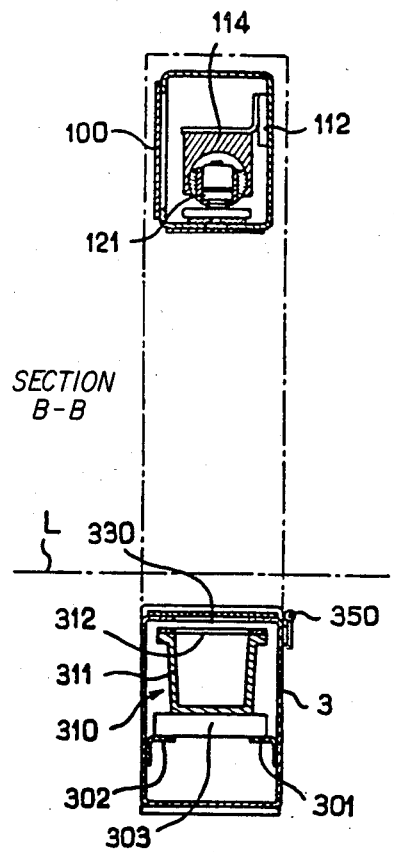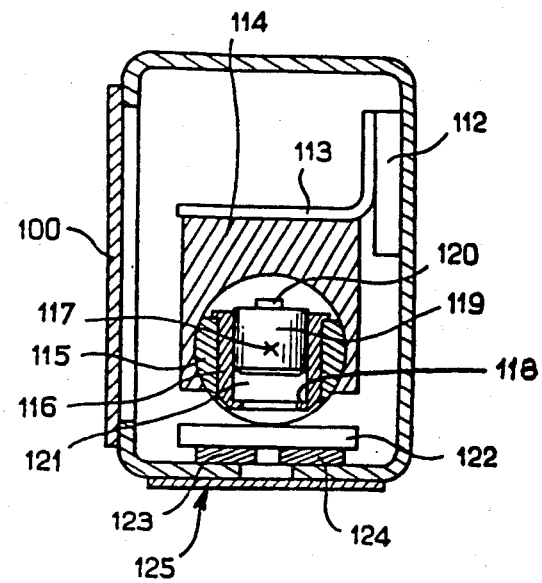
FIG.5   FIG.6
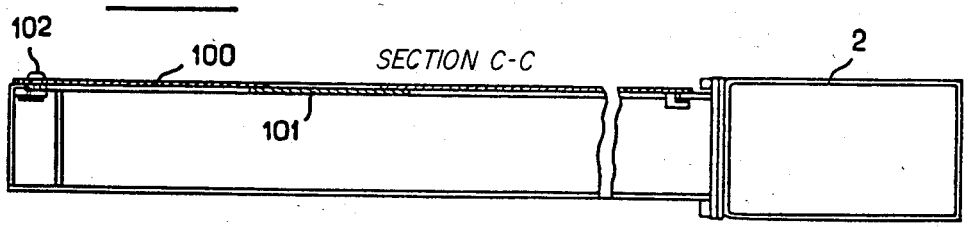
FIG.7
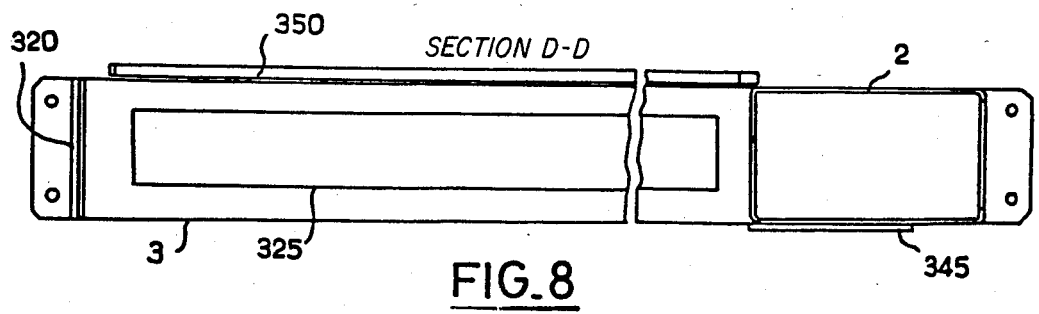
FIG.8

METHOD AND APPARATUS FOR INSPECTION BY RADIOACTIVE GAGE OF A MOVING STRIP OF MATERIAL, IN PARTICULAR A STRIP OF RUBBER FOR TIRES

BACKGROUND OF THE INVENTION

This invention relates to inspection continuously and without contact of a moving strip of material, in particular a strip of rubber intended for the manufacture of tires.

Such strips are produced by a machine such as an extruder associated with a die giving the desired shape to the rubber strip.

They must be inspected to detect variations of mass therein, notably air inclusions, which would render them unsuitable for the manufacture of tires.

Inspection by mechanical weighing has been tried, using a support roller for the moving strip. The efficacy and precision o this method of inspection, some hundredths in relative terms, are not really satisfactory. Furthermore, as the strip is carried away from the extruder by a mechanised belt, the pull tends to perturb the mechanical weighing.

Besides, it is not technically desirable to place the support roller for weighing very close to the extruder. In fact, the rubber strip emerges from it hot and deformable, at the same time moving around its mean position. Finally, precise and delicate adjustments are necessary each time that the dimensions of the strip are changed, according to the type of tire to be made.

In these circumstances, the object of the invention is to measure the mass per unit length of the moving rubber strip.

Equally, the object of the invention is to detect without contact very slight localised variations in weight, down to some thousandths in relative terms, of a moving strip of material.

The object of the invention is also to enable this precision to be maintained, even in the presence of displacements of the moving strip of material around its mean line of travel.

Another object of the invention is to effect said detection in difficult working conditions: the moving material still being hot on exit from the extruder; and a corrosive environment, with sulfur present.

Finally, it is an object of the invention to adapt the measurement easily to strips of different width and/or profile, corresponding for example to different types of tires to be made.

SUMMARY OF THE INVENTION

To these ends, the invention provides first a method for inspection of a moving strip of material, in particular a strip of rubber, using an ionising-radiation gage, operating in a measurement plane transverse to the axis of movement of the strip.

In this method, there are provided, on one side of the zone of passage of the strip through the measurement plane, two substantially pointlike, collimated, identical sources of ionising radiation positioned and oriented to define a substantially constant flux of radiation at the level of the zone of passage of the strip, the resulting beam of radiation extending beyond the said zone of passage on both sides, and, on the other side, adjacent the said zone of passage, detecting means having an elongate active face, disposed to receive substantially all the emitted radiation. At the same time, the variations as the strip moves of the output signal of the detecting means are monitored.

This enables detection without contact, with high precision, of localised internal air inclusions in the strip, independently of fluctuations in the position thereof around its mean zone of passage. It has been found that the appropriate use of several sources enables slight localised variations in mass of the rubber strip to be detected, even when it is subject to small displacements in a plane perpendicular to its axis of movement.

The term "flux" is defined in a Recommendation of the International Electrotechnic Commission (publication 476; 1st edition 1974): "Flux (of particles): At a given point in space, the quotient of the number dN of particles which in a given time interval enter a suitably small sphere centred at this point, divided by the area da of the great circle of this sphere: phi=dN/da." As is often done by those skilled in the art, the word "flux" is used here for electromagnetic radiation (photons) as well as for particles, alpha or beta for example.

It should be noted that in theory the flux is constant only at a given moment. It varies as a function of time with the weakening in level of activity of the radioactive sources involved. However, in the case of sources with long half-lives (about 450 years for americium 241 for example), the radioactive weakening is negligible. Thus the flux can equally be accepted as constant in relation to time.

The invention also provides an apparatus for inspection of a moving strip of material, in particular a strip of rubber, comprising a support frame with two parallel arms which contain respectively maskable means for emitting ionising radiation and means for detecting ionising radiation, these two means defining together a measurement plane where the emitted radiation traverses the strip thereafter to be received by the detecting means.

According to the invention, the emitting means comprises two substantially pointlike, collimated, identical sources of ionising radiation positioned and oriented to define a substantially constant flux of radiation at the level of the zone of passage of the strip in the measurement plane, the resulting beam of radiation extending beyond the said zone of passage on both sides, and the detecting means is provided with an elongate active face, disposed transversely adjacent the said zone of passage to receive substantially all the emitted radiation.

This enables, by monitoring of the variations of the output signal of the ionisation chamber, detection without contact, with high precision, of localised internal air inclusions in the strip, independently of fluctuations in the position thereof around its mean zone of passage.

Preferably, the two sources are disposed on a common parallel to the large transverse dimension of the strip, and spaced substantially by the width thereof. The two sources may have substantially the same level of activity and the same spatial distribution of radiation. In practice, the measurement plane is usually substantially perpendicular to the axis of movement of the strip.

In one preferred embodiment, the support frame is generally C-shaped, the upper arm thereof containing the two radioactive sources, and the lower arm containing the ionisation chamber.

BRIEF DESCRIPTION OF THE DRAWINGS

Other characteristics and advantages of the invention will appear from the detailed description which follows and from the accompanying drawings, in which:

FIG. 1 illustrates schematically a known arrangement for inspection of a rubber strip intended for manufacture of tires;

FIG. 2 is a diagram illustrating the method according to the invention;

FIG. 3 is a longitudinal sectional view of the apparatus according to the invention;

FIG. 4 is a view from the right as seen in FIG. 3, with door 212 removed, and showing the section line A—A along which the view of FIG. 3 is taken;

FIG. 5 is a section along the line B—B of FIG. 3, whereas FIG. 6 shows a detail of the upper part of FIG. 5; and FIGS. 7 and 8 are sections along the lines C—C (with internal components removed) and D—D of FIG. 3, respectively.

DESCRIPTION OF THE PREFERRED EMBODIMENT

FIG. 1 shows schematically an extruder with a die EXT, which produces a strip of rubber supported by rollers and then by a mechanical belt. It is fed towards a receiving device TRF, which provides treatment with cooling. The general form in cross-section of the strip B is illustrated in FIG. 3, and can be defined as a trapezoid or a very flat triangle. In practice, strips intended for the manufacture of tires can have grooves along their whole length. Their nominal width can be up to 550 mm, and their nominal thickness up to 40 mm.

It is known to place weighing equipment EQP along the path of the strip, equipped with a roller (or several) over which the strip passes. The major problem with this arrangement is its lack of precision, because the supporting force applied to the roller involves a length of strip on each side of the roller which is not insignificant. The measurement of this supporting force thus gives low-sensitivity results, as regards the presence of air inclusions (or of excess weights) at any given point in the strip.

Other difficulties with the use of such weighing equipment have already been indicated above.

The present invention provides appropriate precision, by an improvement in ionising-radiation gages.

Thus the equipment EQP of FIG. 1 is replaced by a gage (FIG. 2) with radioactive sources 121 and 141 and a detector such as an ionisation chamber 310, operating in a measurement plane transverse to the axis of movement of the strip, preferably substantially perpendicular thereto. In practice, the gage can be placed closer to the extruder than the equipment EQP is; and rollers, simply for support, are placed as required upstream and downstream. The sources and the ionisation chamber can be provided with thin sheets of material, so-called windows, in the path of the radiation.

According to the invention, there are thus provided, on one side of the zone of passage of the strip B through the measurement plane, two substantially pointlike, collimated, identical radioactive sources 121 and 141, having substantially the same level of activity and the same spatial distribution of radiation, positioned and oriented to define a substantially constant flux of radiation at the level of the zone of passage of the strip, the resulting beam of radiation extending beyond the said zone of passage on both sides, and, on the other side, adjacent the said zone of passage, a single elongate ionisation chamber 310, disposed to receive substantially all the emitted radiation. The variations as the strip moves of the output signal of the ionisation chamber are monitored, whereby to detect without contact, with high precision, localised internal air inclusions in the strip (or excess weight) independently of fluctuations in the position thereof around its mean zone of passage.

The sources 121 and 141 have substantially the same level of activity, and a generally bell-shaped spatial distribution of radiation, nearly symmetrical about an axis (naturally with statistical fluctuations). They are disposed on a common parallel to the line of passage (L), and their spacing is of the order of the width of the strip. By making the beams of the two sources intersect, and their axes of radiation slightly converge, by an angle theta of about 10° relative to the vertical, and by suitably positioning the sources 121 and 141, it has been found that the precision of detection of variations in weight gets down to some thousandths, even in the presence of small displacements of the strip laterally and, above all, vertically. A substantially constant flux of radiation is obtained at the level of the zone of passage, or more precisely of the line of passage L of the strip B, over the whole width of the strip, by appropriate choice of the parameters defining the radiation.

In the currently preferred embodiment, the sources are of americium 241, which produces X-rays and/or gamma rays. As alternatives, there can be used:
 as sources of X-rays, plutonium 238 or curium 244,
 as sources of gamma rays, cesium 137 or cobalt 60,
 as sources of beta rays (particles), strontium 90, krypton 85 or promethium 147.

The ionisation chamber is filled with gas, which can be xenon, argon or again krypton.

The apparatus according to the invention will now be described in detail with reference to FIGS. 3 to 8.

In the general view of FIG. 3, the apparatus comprises a generally C-shaped support frame, with a vertical column 2, and upper and lower arms 1 and 3 the spacing of which is adjustable, in this case by movement of the connection of the arm 1 to the column 2.

Essentially, the upper arm 1 houses two source carriers 111 and 131. These are secured to respective support plates 112 and 132, enabling their position to be adjusted horizontally and vertically.

The lower arm 3 contains (FIGS. 3 and 5) the ionisation chamber 310, comprising a long conductive trough 311, with a slightly diverging U-shaped cross-section, enclosing a tubular anode (not shown) and closed at the top by a thin plate 312, also conductive, of light alloy. The chamber 310 is filled with a rare gas at a pressure of 1 to 2 bars. Its trough 311 rests on isolating transverse beams 303 and 304, which are supported in turn on angle-irons 301 and 302 secured internally in the arm 3.

The ionisation chamber is coupled to an electronic circuit, or measuring head 340, comprising a high voltage supply 341 (500 to 2000 volts) and a preamplifier 342. The high voltage supply maintains the wall of the chamber at a negative voltage relative to the anode. The preamplifier amplifies the very weak current ($10^{-8}$ to $10^{-12}$ amperes) flowing in the chamber and converts it to a voltage. The transformed signal is usable by any electronic circuitry, analog or digital.

On its right-hand face (FIGS. 3 and 4), the apparatus has an electrical connector 222 for the measuring head 340. A connector 221 is coupled to the sources by a lead extending through the column 2 to a feed-through 215 which leads into the upper arm 1. Finally, the right-hand face receives a compressed air supply at 223 (FIG. 4) coupled to an air-tight connection 214 which leads into the upper arm 1 (generally the air-tubes and electric leads are not shown).

The compressed air is fed by a pressure-reducing valve 157 to an electric valve 156 which, under the control of the signals applied through connector 221, mechanically moves with jacks (not shown) the source carriers 111 and 131 to the measuring position (indicator 159 illuminated) or to the protected position (no air, indicator 158 illuminated). The sources are masked when the valve 155 is in the "safety" position.

This compressed air can also be used to provide overpressure in the upper arm 1 and the lower arm 3.

Finally, the arm 1 is provided with oblong apertures in line with the source carriers 111 and 131, covered with thin sheets of light alloy, forming the windows referenced 125 and 145.

Various access doors, sealed by butt joints, are provided: a door 100 with a lock 102 (FIG. 7) on the front face of the arm 1, with a window in line with the valve 155; doors 211 and 212 (FIG. 3) on the left side of the column 2 (the doors 211 and 212 are omitted in FIG. 4); a door 320 (FIG. 3) for the installation of the ionisation chamber; a door 345 (FIG. 8) in line with the electronic circuitry.

The two source carriers being identical, and mounted symmetrically, only the source carrier 111 will be described in detail, with reference to FIG. 6.

The support plate 112 holds a block 114 on a right-angle bracket 113, forming a radiation screen and having an internal cylindrical bore with its axis parallel to the large dimension of the arm 1. An assembly 115, 116 within this bore, pivoting about an axis 117, holds the source proper 121, urged against a shoulder 118 in the part 116 by a body 119 and a clamp 120.

Under the source, collimation is obtained by two strips 123 and 124 secured by plates 122. This collimator is placed in line with the oblong opening in the arm and with the window 125. Thus a thin fan of radiation is obtained, corresponding in width to the bell-shaped spatial distribution of radiation already discussed.

The position of the source carriers is adjusted so that in the measuring position they have a predetermined angular orientation relative to the vertical. This angle theta is adjusted to obtain the prescribed condition of constant flux, taking into account the geometry defined by the sources, the line of passage, the usable length of the ionisation chamber, and the maximum width of the measured strip. The range of usable angles of inclination is between $-20°$ (divergent) and $+30°$ (convergent) to the vertical.

In line with the upper face 312 of the ionisation chamber 310, the lower arm 3 is provided with an opening 325 (FIG. 8), also covered with a window of light alloy, referenced 330 (FIG. 5). Finally, the compressed air is supplied to a duct 350, provided with apertures along its length to ensure the absence of particles on the window 330.

An apparatus of the type described has been made for the detection of air inclusions in rubber strips for tires, the nominal width of which is up to 550 mm and the nominal thickness up to 40 mm. The measurement of variations in mass obtained is better than 0.2% over the whole range, for variations in the line of passage of $\pm 3$ mm. Such precision provides a good basis for control of an extruder upstream.

The specific characteristics of this exemplary embodiment are as follows:

2 sources of americium 241 (X-rays and/or gamma rays, 60 keV) of 1 Ci, collimated by a window adjustable from 0.2 to 1 cm;

windows for the sources of aluminium of about 100 microns in thickness;

ionisation chamber with interior dimensions of 750 mm in length, 80 mm in width and 80 mm in height, with longitudinal anode, filled with xenon at 1.5 bars;

window 312 of the chamber of mylar metallised to a thickness of 350 microns;

window 330 of aluminium of about 100 microns in thickness;

source axis spacing adjustable around 550 mm;

actual clearance between sources and chamber adjustable around 400 mm;

height of the line of passage above the chamber 30 mm;

angle theta, adjustable, in a range from about $-20°$ to $+30°$.

In conjunction with an appropriate adjustment of the source positions, laterally and vertically, an appropriate choice of the angle theta allows the prescribed conditions to be attained with precision.

Experiments have shown that the use of two sources in accordance with the invention provides a remarkable insensitivity to lateral and vertical displacements of the strip, even if its means position is shifted laterally with respect to the axis of symmetry of the two sources.

It has been found that this corresponds to a condition of substantially constant flux of radiation from the two sources, at the level of the line of passage.

Although no arrangment with more than two sources has been tried, it appears possible to obtain a substantially constant flux in such a way as well, and thus the advantages of the present invention (precision and insensitivity to displacements).

The actual application of the present invention is to the detection of air inclusions in rubber strips intended for the manufacture of tires. However, other applications can be envisaged:

detection of localised overweights. It may be noted that, as for the detection of air or other inclusions, the detection or overweights presumes that the geometry of the strip in cross section as well as its density should be constant;

more generally, the measurement of the mass per unit length of a moving strip product.

In this respect, the present invention encompasses all variations in the described implementation which fall within the scope of the appended claims.

We claim:

1. Method for inspection of a moving strip of material, in particular a strip of rubber, using an ionising-radiation gage, operating in a measurement plane transverse to the axis of movement of the strip, wherein there are provided on one side of the zone of passage of the strip through the measurement plane, two substantially pointlike, collimated, identical sources of ionising radiation positioned and oriented to define a substantially constant flux of radiation at the level of the zone of passage of the strip, the resulting beam of radiation extending beyond the said zone of passage on both sides, and, on the other side, adjacent the said zone of passage, detecting means having an elongate active face, disposed to receive substantially all the emitted radiation, and wherein the variations as the strip moves of the output signal of the detecting means are monitored, whereby to detect without contact and with high precision slight variations in mass of the strip, in particular localised air inclusions, independently of fluctuations in the position of the strip around its mean zone of passage.

2. Method according to claim 1, wherein the two sources are disposed on a common parallel to the large transverse dimension of the strip, and spaced substantially by the width thereof.

3. Method according to claim 1, wherein the two sources have substantially the same level of activity and the same spatial distribution of radiation.

4. Method according to claim 1, wherein the measurement plane is substantially perpendicular to the axis of movement of the strip.

5. Method according to claim 1, wherein the souces of radiation are X-ray or gamma ray sources.

6. Method according to claim 5, wherein the sources of radiation are of americium 241.

7. Apparatus for inspection of a moving strip of material, in particular a strip of rubber, comprising a support frame with two parallel arms which contain respectively maskable means for emitting ionising radiation and means for detecting ionising radiation, these two means defining together a measurement plane where the emitted radiation traverses the strip thereafter to be received by the detecting means, wherein the emitting means comprises two substantially pointlike, collimated, identical sources of ionising radiation positioned and oriented to define a substantially constant flux of radiation at the level of the zone of passage of the strip in the measurement plane, the resulting beam of radiation extending beyond the said zone of passage on both sides, and wherein the detecting means is provided with an elongate active face, disposed transversely adjacent the said zone of passage to receive substantially all the emitted radiation, whereby to enable by monitoring of the variations of the output signal of the ionisation chamber detection without contact, with high precision, of localised internal air inclusions in the strip, independently of fluctuations in the position thereof around its mean zone of passage.

8. Apparatus according to claim 7, wherein the two sources are disposed on a common parallel to the large transverse dimension of the strip, and spaced substantially by the width thereof.

9. Apparatus according to claim 7, wherein the two sources have substantially the same level of activity and the same spatial distribution of radiation.

10. Apparatus according to claim 7, wherein the measurement plane is substantially perpendicular to the axis of movement of the strip.

11. Apparatus according to claim 7, wherein the sources of radiation are X-ray or gamma ray sources.

12. Apparatus according to claim 11, wherein the sources of radiation are of americium 241.

13. Apparatus according to claim 7, wherein the support frame is generally C-shaped, the upper arm thereof containing the two radioactive sources, and the lower arm containing the detecting means.

14. Apparatus according to claim 7, wherein the detecting means comprises a single elongate ionisation chamber.

15. Apparatus according to claim 7, wherein the upper arm and the lower arm are adjustable in relative position, as are the position and orientation of the sources in the upper arm.

* * * * *